United States Patent
Tang et al.

(10) Patent No.: US 9,279,110 B2
(45) Date of Patent: Mar. 8, 2016

(54) POLYNUCLEOTIDES ENCODING POLYPEPTIDES HAVING PHOSPHOLIPASE C ACTIVITY

(75) Inventors: Lan Tang, Beijing (CN); Ye Liu, Beijing (CN); Kim Borch, Birkeroed (DK); Jesper Brask, Vaerloese (DK)

(73) Assignee: Novozymes A/S, Bagsvaerd (DK)

( * ) Notice: Subject to any disclaimer, the term of this patent is extended or adjusted under 35 U.S.C. 154(b) by 134 days.

(21) Appl. No.: 13/884,063

(22) PCT Filed: Nov. 9, 2011

(86) PCT No.: PCT/EP2011/069770
§ 371 (c)(1),
(2), (4) Date: Aug. 8, 2013

(87) PCT Pub. No.: WO2012/062817
PCT Pub. Date: May 18, 2012

(65) Prior Publication Data
US 2013/0309751 A1    Nov. 21, 2013

Related U.S. Application Data

(60) Provisional application No. 61/420,912, filed on Dec. 8, 2010.

(30) Foreign Application Priority Data

Nov. 12, 2010    (WO) ................ PCT/CN2010/078674

(51) Int. Cl.
| | | |
|---|---|---|
| C07H 21/04 | (2006.01) |
| C12N 15/00 | (2006.01) |
| C12N 1/14 | (2006.01) |
| C12N 1/20 | (2006.01) |
| C12N 5/04 | (2006.01) |
| C12N 5/07 | (2010.01) |
| C12P 21/02 | (2006.01) |
| C12N 9/20 | (2006.01) |
| C11B 3/00 | (2006.01) |

(52) U.S. Cl.
CPC . *C12N 9/20* (2013.01); *C11B 3/003* (2013.01); *C12Y 301/04003* (2013.01)

(58) Field of Classification Search
None
See application file for complete search history.

(56) References Cited

U.S. PATENT DOCUMENTS

2005/0108789 A1    5/2005    Gramatikova et al.
2009/0053768 A1*   2/2009    Nagasaki et al. ............ 435/71.2

FOREIGN PATENT DOCUMENTS

WO    2008/094847 A1    8/2008

OTHER PUBLICATIONS

Ciofala et al, Regulatory Toxicol Pharmacol, vol. 45, No. 1, pp. 1-8 (2006).
Dijkstra et al, Eur J Lipid Sci Technol, vol. 112, No. 11, pp. 1178-1189 (2010).
Fedodara et al, Uniprot Acces No. BM076 (2009).
Nagasaki et al, EMBL Acces No. DD402938 (2007).
Nagasaki et al, Geneseq Access No. AEK01032 (2006).

* cited by examiner

*Primary Examiner* — David J Steadman
(74) *Attorney, Agent, or Firm* — Kristin McNamara

(57) ABSTRACT

The present invention relates to isolated polypeptides having phospholipase C activity and isolated polynucleotides encoding the polypeptides. The invention also relates to nucleic acid constructs, vectors, and host cells comprising the polynucleotides as well as methods of producing and using the polypeptides.

7 Claims, No Drawings

SEQUENCE LISTING

<160> NUMBER OF SEQ ID NOS: 2

<210> SEQ ID NO 1
<211> LENGTH: 1932
<212> TYPE: DNA
<213> ORGANISM: Kinochaeta sp
<220> FEATURE:
<221> NAME/KEY: CDS
<222> LOCATION: (1)..(1929)
<220> FEATURE:
<221> NAME/KEY: sig_peptide
<222> LOCATION: (1)..(54)
<220> FEATURE:
<221> NAME/KEY: mat_peptide
<222> LOCATION: (55)..(1929)

<400> SEQUENCE: 1

```
atg cgt gcc tcc tcg att ctt tcg ctg gct ctg ggc ctc tcg gtt gcc      48
Met Arg Ala Ser Ser Ile Leu Ser Leu Ala Leu Gly Leu Ser Val Ala
        -15                 -10                  -5 cag gcc gct gtg aac ccc gcc gat gtc ctg tct gtt gtg gag aag cga      96
Gln Ala Ala Val Asn Pro Ala Asp Val Leu Ser Val Val Glu Lys Arg
    -1   1               5                  10 gtc gac ccg gct agc ggc cta gag gtg cgc agc att tgg gac acc atc     144
Val Asp Pro Ala Ser Gly Leu Glu Val Arg Ser Ile Trp Asp Thr Ile
 15                  20                  25                  30 tgg aac gac att aaa tcg gcg gcc gac tgt act gcc tgc gag gcc gtc     192
Trp Asn Asp Ile Lys Ser Ala Ala Asp Cys Thr Ala Cys Glu Ala Val
                 35                  40                  45 ttg act ctg ctc aag ggc gtc gcg gcc ttt ggc gat aat ttt ttc gta     240
Leu Thr Leu Leu Lys Gly Val Ala Ala Phe Gly Asp Asn Phe Phe Val
             50                  55                  60 gag gtt ttg acc gag atc tgt gac ctt tcc ggg gct gag gat gat gat     288
Glu Val Leu Thr Glu Ile Cys Asp Leu Ser Gly Ala Glu Asp Asp Asp
         65                  70                  75 gtg tgc tcc ggt gtt ctt agc ctc gag ggc cca atc ata gcc aac gat     336
Val Cys Ser Gly Val Leu Ser Leu Glu Gly Pro Ile Ile Ala Asn Asp
 80                  85                  90 atc cgt aag atg agc att ggc tcc aag aca tca gag ctc ttc tgc atc     384
Ile Arg Lys Met Ser Ile Gly Ser Lys Thr Ser Glu Leu Phe Cys Ile
 95                 100                 105                 110 acc ttc ctg gga ctg tgc tcg tac ccg gcg gtg gac gct ttc acc gtc     432
Thr Phe Leu Gly Leu Cys Ser Tyr Pro Ala Val Asp Ala Phe Thr Val
                115                 120                 125 ccc ttc ccg acc gcg aag tca gcc gcc acc cgg ccc gtg tcg tcg ggc     480
Pro Phe Pro Thr Ala Lys Ser Ala Ala Thr Arg Pro Val Ser Ser Gly
            130                 135                 140 aaa gac ccc atc tac gtc gtg cac tac tct gac atc cac atc gat ccc     528
Lys Asp Pro Ile Tyr Val Val His Tyr Ser Asp Ile His Ile Asp Pro
        145                 150                 155 ttc tat gtg gca gga tcc gcc agc aac tgc acc aag ccc atc tgc tgc     576
Phe Tyr Val Ala Gly Ser Ala Ser Asn Cys Thr Lys Pro Ile Cys Cys
    160                 165                 170 cga gat tac act tcg gcg tcg tcc ccg ggc aac aac aac tcc cct gcc     624
Arg Asp Tyr Thr Ser Ala Ser Ser Pro Gly Asn Asn Asn Ser Pro Ala
175                 180                 185                 190 ggc ccg tac ggc gac cac aac tgc gac gtc ccg att agc ctg gag gac     672
Gly Pro Tyr Gly Asp His Asn Cys Asp Val Pro Ile Ser Leu Glu Asp
                195                 200                 205 agc atg tat gct gcc atc aag aag ctg gtg cct gat gcc gcc ttc ggc     720
Ser Met Tyr Ala Ala Ile Lys Lys Leu Val Pro Asp Ala Ala Phe Gly
            210                 215                 220
```

|  |  |
|---|---|
| atc ttt act ggc gat att gtc gac cac gcc gtc tgg aat acc tcg gag<br>Ile Phe Thr Gly Asp Ile Val Asp His Ala Val Trp Asn Thr Ser Glu<br>          225                    230                    235 | 768 |
| agt cag aac atc atc gac atg aat gac gcc tac acg cgc atg aag aac<br>Ser Gln Asn Ile Ile Asp Met Asn Asp Ala Tyr Thr Arg Met Lys Asn<br>240                    245                    250 | 816 |
| tcg ggc atg ctg ccg acc atc ttc gcc acg gcg ggc aac cat gaa gcg<br>Ser Gly Met Leu Pro Thr Ile Phe Ala Thr Ala Gly Asn His Glu Ala<br>255                    260                    265                    270 | 864 |
| tcg ccc gtc aac tcg ttc ccg ccg gcc atc ggc aac gag tcg cag<br>Ser Pro Val Asn Ser Phe Pro Pro Ala Ile Gly Asn Glu Ser Gln<br>                    275                    280                    285 | 912 |
| tgg gtt tac gac aca ctg gcc agc gac tgg agc cag tgg atc ggc acg<br>Trp Val Tyr Asp Thr Leu Ala Ser Asp Trp Ser Gln Trp Ile Gly Thr<br>                    290                    295                    300 | 960 |
| tcg ggc gcg agc tcg gtc gag tcc atc ggc gct tac agc gtg cag tac<br>Ser Gly Ala Ser Ser Val Glu Ser Ile Gly Ala Tyr Ser Val Gln Tyr<br>305                    310                    315 | 1008 |
| ggc agc acc aag ctg cgc gtc atc tcg ctc aac acc aac atg tac tac<br>Gly Ser Thr Lys Leu Arg Val Ile Ser Leu Asn Thr Asn Met Tyr Tyr<br>    320                    325                    330 | 1056 |
| atc gag aac ttc tac ctc tat gag ccc acc atg gag caa gat cca gcc<br>Ile Glu Asn Phe Tyr Leu Tyr Glu Pro Thr Met Glu Gln Asp Pro Ala<br>335                    340                    345                    350 | 1104 |
| ggg cag ttc gcc tgg ctc gtg tcc gag ctg agc gcc gcc gaa gcc gcc<br>Gly Gln Phe Ala Trp Leu Val Ser Glu Leu Ser Ala Ala Glu Ala Ala<br>                    355                    360                    365 | 1152 |
| ggc gag cgc gtg tgg atc atc ggc cac atg ccg ctg ggt ctc tcg gac<br>Gly Glu Arg Val Trp Ile Ile Gly His Met Pro Leu Gly Leu Ser Asp<br>                    370                    375                    380 | 1200 |
| gcc ttc cac gac ccg agc aac tac ttt gac cag atc gtc aac cgc tac<br>Ala Phe His Asp Pro Ser Asn Tyr Phe Asp Gln Ile Val Asn Arg Tyr<br>                  385                    390                    395 | 1248 |
| gag gcc acc atc gcc gcc atg ttc ttc ggc cac acc cac gag gac cat<br>Glu Ala Thr Ile Ala Ala Met Phe Phe Gly His Thr His Glu Asp His<br>                400                    405                    410 | 1296 |
| ttc cag atc tcg tac tcg gac tac aac gcc cgc acg gcc gcc aac gcc<br>Phe Gln Ile Ser Tyr Ser Asp Tyr Asn Ala Arg Thr Ala Ala Asn Ala<br>415                    420                    425                    430 | 1344 |
| cgc gcc gtc tcc tac atc atg ccg tcg ctg acg ccg acc tcg ggc cac<br>Arg Ala Val Ser Tyr Ile Met Pro Ser Leu Thr Pro Thr Ser Gly His<br>                  435                    440                    445 | 1392 |
| ccg acc ttc cgc gtc tac acg gtc gac ccc gag acc ttc ggc gtg ctg<br>Pro Thr Phe Arg Val Tyr Thr Val Asp Pro Glu Thr Phe Gly Val Leu<br>                    450                    455                    460 | 1440 |
| gac gcg acg acc tac tac gcc gac atg tcg cag ccg acc tac cag acc<br>Asp Ala Thr Thr Tyr Tyr Ala Asp Met Ser Gln Pro Thr Tyr Gln Thr<br>                  465                    470                    475 | 1488 |
| gcg ggg ccg gcc tgg tcc gtc tac tac agc gcc aag gcc gcc tac ggc<br>Ala Gly Pro Ala Trp Ser Val Tyr Tyr Ser Ala Lys Ala Ala Tyr Gly<br>                480                    485                    490 | 1536 |
| ggg ctc gtc gac ccg ccc gtc gcc gcc gac gac gcc gcc gag ctg<br>Gly Leu Val Asp Pro Pro Val Ala Ala Asp Asp Ala Ala Glu Leu<br>495                    500                    505                    510 | 1584 |
| acg ccc gcc ttc tgg cac aac gtg acg gcc gcg ctg gcc gcc gac ccg<br>Thr Pro Ala Phe Trp His Asn Val Thr Ala Ala Leu Ala Ala Asp Pro<br>                  515                    520                    525 | 1632 |
| gcc agc ttc gac gcc tac tac gcg cgc aag acg cgc ggc tgg gac gtg<br>Ala Ser Phe Asp Ala Tyr Tyr Ala Arg Lys Thr Arg Gly Trp Asp Val<br>                    530                    535                    540 | 1680 |

```
gcc gcc tgc gcc ggc gcc tgc gcg gcc gcc gag gtc tgc gcc ctg cgc    1728
Ala Ala Cys Ala Gly Ala Cys Ala Ala Ala Glu Val Cys Ala Leu Arg
        545                 550                 555 gcc gcc cgc gcc cag gac aac tgc gtc gtg ccc acg ccc ggc gtg cac    1776
Ala Ala Arg Ala Gln Asp Asn Cys Val Val Pro Thr Pro Gly Val His
    560                 565                 570 ttc agc aag cgc gcc gac gag ggc acc ctg gcc cac cac cgc gac gag    1824
Phe Ser Lys Arg Ala Asp Glu Gly Thr Leu Ala His His Arg Asp Glu
575                 580                 585                 590 tgc ggc gtc agc gtc gcc cgc aac agc ctc tcc agc ctc gtc gtg cag    1872
Cys Gly Val Ser Val Ala Arg Asn Ser Leu Ser Ser Leu Val Val Gln
                595                 600                 605 cgc gag gcg ctg gag cac ctc gag ggc cgc ctg agc gag aag cgg agg    1920
Arg Glu Ala Leu Glu His Leu Glu Gly Arg Leu Ser Glu Lys Arg Arg
            610                 615                 620 atg gcc gtg tga                                                     1932
Met Ala Val
        625

<210> SEQ ID NO 2
<211> LENGTH: 643
<212> TYPE: PRT
<213> ORGANISM: Kinochaeta sp

<400> SEQUENCE: 2

Met Arg Ala Ser Ser Ile Leu Ser Leu Ala Leu Gly Leu Ser Val Ala
        -15                 -10                 -5

Gln Ala Ala Val Asn Pro Ala Asp Val Leu Ser Val Val Glu Lys Arg
    -1  1                   5                   10

Val Asp Pro Ala Ser Gly Leu Glu Val Arg Ser Ile Trp Asp Thr Ile
15                  20                  25                  30

Trp Asn Asp Ile Lys Ser Ala Ala Asp Cys Thr Ala Cys Glu Ala Val
                35                  40                  45

Leu Thr Leu Leu Lys Gly Val Ala Ala Phe Gly Asp Asn Phe Phe Val
            50                  55                  60

Glu Val Leu Thr Glu Ile Cys Asp Leu Ser Gly Ala Glu Asp Asp
65                  70                  75

Val Cys Ser Gly Val Leu Ser Leu Glu Gly Pro Ile Ile Ala Asn Asp
        80                  85                  90

Ile Arg Lys Met Ser Ile Gly Ser Lys Thr Ser Glu Leu Phe Cys Ile
95                  100                 105                 110

Thr Phe Leu Gly Leu Cys Ser Tyr Pro Ala Val Asp Ala Phe Thr Val
                115                 120                 125

Pro Phe Pro Thr Ala Lys Ser Ala Ala Thr Arg Pro Val Ser Ser Gly
            130                 135                 140

Lys Asp Pro Ile Tyr Val Val His Tyr Ser Asp Ile His Ile Asp Pro
        145                 150                 155

Phe Tyr Val Ala Gly Ser Ala Ser Asn Cys Thr Lys Pro Ile Cys Cys
    160                 165                 170

Arg Asp Tyr Thr Ser Ala Ser Ser Pro Gly Asn Asn Ser Pro Ala
175                 180                 185                 190

Gly Pro Tyr Gly Asp His Asn Cys Asp Val Pro Ile Ser Leu Glu Asp
                195                 200                 205

Ser Met Tyr Ala Ala Ile Lys Lys Leu Val Pro Asp Ala Ala Phe Gly
            210                 215                 220

Ile Phe Thr Gly Asp Ile Val Asp His Ala Val Trp Asn Thr Ser Glu
        225                 230                 235
```

```
Ser Gln Asn Ile Ile Asp Met Asn Asp Ala Tyr Thr Arg Met Lys Asn
240                 245                 250

Ser Gly Met Leu Pro Thr Ile Phe Ala Thr Ala Gly Asn His Glu Ala
255                 260                 265                 270

Ser Pro Val Asn Ser Phe Pro Pro Ala Ile Gly Asn Glu Ser Gln
                275                 280                 285

Trp Val Tyr Asp Thr Leu Ala Ser Asp Trp Ser Gln Trp Ile Gly Thr
                290                 295                 300

Ser Gly Ala Ser Ser Val Glu Ser Ile Gly Ala Tyr Ser Val Gln Tyr
                305                 310                 315

Gly Ser Thr Lys Leu Arg Val Ile Ser Leu Asn Thr Asn Met Tyr Tyr
320                 325                 330

Ile Glu Asn Phe Tyr Leu Tyr Glu Pro Thr Met Glu Gln Asp Pro Ala
335                 340                 345                 350

Gly Gln Phe Ala Trp Leu Val Ser Glu Leu Ser Ala Ala Glu Ala Ala
                355                 360                 365

Gly Glu Arg Val Trp Ile Ile Gly His Met Pro Leu Gly Leu Ser Asp
                370                 375                 380

Ala Phe His Asp Pro Ser Asn Tyr Phe Asp Gln Ile Val Asn Arg Tyr
        385                 390                 395

Glu Ala Thr Ile Ala Ala Met Phe Phe Gly His Thr His Glu Asp His
400                 405                 410

Phe Gln Ile Ser Tyr Ser Asp Tyr Asn Ala Arg Thr Ala Ala Asn Ala
415                 420                 425                 430

Arg Ala Val Ser Tyr Ile Met Pro Ser Leu Thr Pro Thr Ser Gly His
                435                 440                 445

Pro Thr Phe Arg Val Tyr Thr Val Asp Pro Glu Thr Phe Gly Val Leu
                450                 455                 460

Asp Ala Thr Thr Tyr Tyr Ala Asp Met Ser Gln Pro Thr Tyr Gln Thr
                465                 470                 475

Ala Gly Pro Ala Trp Ser Val Tyr Tyr Ser Ala Lys Ala Ala Tyr Gly
                480                 485                 490

Gly Leu Val Asp Pro Pro Val Ala Ala Asp Ala Ala Ala Glu Leu
495                 500                 505                 510

Thr Pro Ala Phe Trp His Asn Val Thr Ala Ala Leu Ala Ala Asp Pro
                515                 520                 525

Ala Ser Phe Asp Ala Tyr Tyr Ala Arg Lys Thr Arg Gly Trp Asp Val
                530                 535                 540

Ala Ala Cys Ala Gly Ala Cys Ala Ala Glu Val Cys Ala Leu Arg
                545                 550                 555

Ala Ala Arg Ala Gln Asp Asn Cys Val Val Pro Thr Pro Gly Val His
                560                 565                 570

Phe Ser Lys Arg Ala Asp Glu Gly Thr Leu Ala His His Arg Asp Glu
575                 580                 585                 590

Cys Gly Val Ser Val Ala Arg Asn Ser Leu Ser Ser Leu Val Val Gln
                595                 600                 605

Arg Glu Ala Leu Glu His Leu Glu Gly Arg Leu Ser Glu Lys Arg Arg
                610                 615                 620

Met Ala Val
        625
```

POLYNUCLEOTIDES ENCODING POLYPEPTIDES HAVING PHOSPHOLIPASE C ACTIVITY

CROSS-REFERENCE TO RELATED APPLICATIONS

This application is a 35 U.S.C. 371 national application of PCT/EP2011/069770 filed Nov. 9, 2011 which claims priority or the benefit under 35 U.S.C. 119 of Chinese PCT application no. PCT/CN2010/078674 filed Nov. 12, 2010 and U.S. provisional application No. 61/420,912 filed Dec. 8, 2010 the contents of which are fully incorporated herein by reference.

REFERENCE TO A SEQUENCE LISTING

This application contains a Sequence Listing in computer readable form, which is incorporated herein by reference.

FIELD OF THE INVENTION

The present invention relates to an enzyme having phospholipase C activity, a cloned DNA sequence encoding the enzyme having phospholipase C activity, a method of producing the enzyme, and the use of said enzyme for a number of industrial applications.

Further, the present invention relates to a method for reducing the content of phosphorous containing components in an edible oil comprising a high amount of non-hydratable phosphorus, by the use of the enzyme having phospholipase C activity.

BACKGROUND OF THE INVENTION

Several types of phospholipases are known which differ in their specificity according to the position of the bond attacked in the phospholipid molecule. Phospholipase A1 (PLA1) removes the 1-position fatty acid to produce free fatty acid and 1-lyso-2-acylphospholipid. Phospholipase A2 (PLA2) removes the 2-position fatty acid to produce free fatty acid and 1-acyl-2-lysophospholipid. The term phospholipase B (PLB) is used for phospholipases having both A1 and A2 activity. Phospholipase C (PLC) removes the phosphate moiety to produce 1,2 diacylglycerol and phosphate ester. Phospholipase D (PLD) produces 1,2-diacylglycerophosphate and base group.

Polypeptides having phospholipase activity may be applied in an industrial process, e.g., for refining of vegetable oils. Before consumption vegetable oils are degummed to provide refined storage stable vegetable oils of neutral taste and light color. The degumming process comprises removing the phospholipid components (the gum) from the triglyceride rich oil fraction.

Traditionally, the degumming process has been based on either water extraction, acidic or caustic treatment followed by a separation process. Due to the emulsifying properties of the phospholipid components, the degumming procedure has resulted in a loss of oil i.e. of triglycerides.

Enzymatic degumming reduces the oils loss due to an efficient hydrolysis of the phospholipids which decrease the emulsifying properties. However, present phospholipase A solutions are impaired by a need for a laborious pH adjustment procedure, and a generation of free fatty acids, while the only present commercially available phospholipase C (Purifine of Verenium, see Dijkstra, 101st AOCS Annual Meeting 10. May 2010), is dependent upon the species of the phospholipids in the oil, as it cannot hydrolyze the phosphatides phosphatidic acid and phosphatidyl inositol. Thus phosphatidic acid and phosphatidyl inositol will remain in the oil after the enzymatic degumming and the phospholipase C-treated oil must be further treated with caustic to remove the residual gums.

There is a need for further enzymes having phospholipase activity and suitable for application in enzymatic degumming of edible oils.

SUMMARY OF THE INVENTION

The inventors have isolated a new phospholipase C enzyme from a strain of *Kinochaeta* sp. found 1997 in China. Accordingly, the present invention provides novel polypeptides having phospholipase C activity and polynucleotides encoding the polypeptides. The polypeptides have activity towards the major phospholipids including phosphatidylcholine, phosphatidylethanolamine, phosphatidic acid and phosphatidyl inositol. The polypeptide of the present invention has a relatively low pH optimum and good activity down to pH 4. The low pH optimum is an advantage in enzymatic degumming of vegetable oils under low pH conditions.

The present invention relates to isolated polypeptides having phospholipase C activity selected from the group consisting of:

(a) a polypeptide having at least 60% sequence identity to the mature polypeptide of SEQ ID NO: 2;

(b) a polypeptide encoded by a polynucleotide that hybridizes under medium-high stringency conditions with (i) the mature polypeptide coding sequence of SEQ ID NO: 1, (ii) the genomic DNA sequence comprising the mature polypeptide coding sequence of SEQ ID NO: 1, or (iii) the full-length complementary strand of (i) or (ii);

(c) a polypeptide encoded by a polynucleotide having at least 60% sequence identity to the mature polypeptide coding sequence of SEQ ID NO: 1;

(d) a variant comprising a substitution, deletion, and/or insertion of one or more (several) amino acids of the mature polypeptide of SEQ ID NO: 2; and (e) a fragment of a polypeptide of (a), (b), (c), (d) or (e) that has phospholipase C activity.

The present invention also relates to nucleic acid constructs, expression vectors, and recombinant host cells comprising the polynucleotides; and to methods of producing the polynucleotides.

The present invention also relates to methods of degumming vegetable oil.

DEFINITIONS

Phospholipase C activity: The term "phospholipase C activity" means the activity that catalyzes the reaction: A phosphatidylcholine+$H_2O$=1,2-sn-diacylglycerol+choline phosphate. For purposes of the present invention, phospholipase C activity is determined according to the procedure described in "Materials and Methods". An enzyme having "phospholipase C activity" may belong to EC 3.1.4.3.

The polypeptides of the present invention have at least 20%, e.g., at least 40%, at least 50%, at least 60%, at least 70%, at least 80%, at least 90%, at least 95%, and at least 100% of the phospholipase C activity of the mature polypeptide of SEQ ID NO: 2.

Isolated polypeptide: The term "isolated polypeptide" means a polypeptide that is modified by the hand of man relative to that polypeptide as found in nature. In one aspect, the polypeptide is at least 1% pure, e.g., at least 5% pure, at least 10% pure, at least 20% pure, at least 40% pure, at least 60% pure, at least 80% pure, and at least 90% pure, as determined by SDS-PAGE.

Non-limiting examples of isolated polypeptides include (1) any non-naturally occurring polypeptide, (2) any polypeptide including, but not limited to, any enzyme, variant, nucleic acid, protein, peptide or cofactor, that is at least partially removed from one or more or all of the naturally occurring constituents with which it is associated in nature; (3) any polypeptide modified by the hand of man relative to that polypeptide found in nature; or (4) any polypeptide modified by increasing the amount of the polypeptide relative to other components with which it is naturally associated. An isolated polypeptide may be present in a fermentation broth sample.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 625 of SEQ ID NO: 2. Amino acids −1 to −18 of SEQ ID NO: 2 are a signal peptide.

Mature polypeptide coding sequence: The term "mature polypeptide coding sequence" means a polynucleotide that encodes a mature polypeptide having phospholipase C activity. In one aspect, the mature polypeptide coding sequence is nucleotides 55 to 1929 of SEQ ID NO: 1. Nucleotides 1 to 54 of SEQ ID NO: 1 encode a signal peptide.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16:276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Fragment: The term "fragment" means a polypeptide having one or more (several) amino acids deleted from the amino and/or carboxyl terminus of a mature polypeptide; wherein the fragment has phospholipase C activity. In one aspect, a fragment contains at least 550 amino acid residues (e.g., amino acids 19 to 569 of SEQ ID NO: 2), at least 575 amino acid residues (e.g., amino acids 19 to 594 of SEQ ID NO: 2), and at least 600 amino acid residues (e.g., amino acids 19 to 619 of SEQ ID NO: 2).

Subsequence: The term "subsequence" means a polynucleotide having one or more (several) nucleotides deleted from the 5' and/or 3' end of a mature polypeptide coding sequence; wherein the subsequence encodes a fragment having phospholipase C activity. In one aspect, a subsequence contains at least 1800 nucleotides (e.g., nucleotides 55 to 1855 of SEQ ID NO: 1), e.g., at least 1825 nucleotides (e.g., nucleotides 55 to 1880 of SEQ ID NO: 1) and at least 1850 nucleotides (e.g., nucleotides 55 to 1905 of SEQ ID NO: 1).

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" means a polynucleotide that is modified by the hand of man relative to that polynucleotide as found in nature. In one aspect, the isolated polynucleotide is at least 1% pure, e.g., at least 5% pure, more at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

Substantially pure polynucleotide: The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5' and 3' untranslated regions, such as promoters and terminators. Preferably, the polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

Coding sequence: The term "coding sequence" means a polynucleotide, which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" means all components necessary for the expression of a polynucleotide encoding a polypeptide of the present invention. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of the polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to additional nucleotides that provide for its expression.

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Variant: The term "variant" means a polypeptide having phospholipase C activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

DETAILED DESCRIPTION OF THE INVENTION

Polypeptides Having Phospholipase C Activity

The present invention relates to isolated polypeptides having phospholipase C activity selected from the group consisting of:

(a) a polypeptide having at least 60% sequence identity to the mature polypeptide of SEQ ID NO: 2;

(b) a polypeptide encoded by a polynucleotide that hybridizes under medium-high stringency conditions with (i) the mature polypeptide coding sequence of SEQ ID NO: 1, (ii) the genomic DNA sequence comprising the mature polypeptide coding sequence of SEQ ID NO: 1, or (iii) the full-length complementary strand of (i) or (ii);

(c) a polypeptide encoded by a polynucleotide having at least 60% sequence identity to the mature polypeptide coding sequence of SEQ ID NO: 1;

(d) a variant comprising a substitution, deletion, and/or insertion of one or more (several) amino acids of the mature polypeptide of SEQ ID NO: 2; and (e) a fragment of a polypeptide of (a), (b), (c), (d) or (e) that has phospholipase C activity.

The present invention relates to isolated polypeptides having a sequence identity to the mature polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or even 100% sequence identity to the mature polypeptide of SEQ ID NO: 2; which have phospholipase C activity. In one aspect, the polypeptides differ by no more than ten amino acids, e.g., by five amino acids, by four amino acids, by three amino acids, by two amino acids, and by one amino acid from the mature polypeptide of SEQ ID NO: 2.

A polypeptide of the present invention preferably comprises or consists of the amino acid sequence of SEQ ID NO: 2 or an allelic variant thereof; or is a fragment thereof having phospholipase C activity. In another aspect, the polypeptide comprises or consists of the mature polypeptide of SEQ ID NO: 2.

The present invention also relates to isolated polypeptides having phospholipase C activity that are encoded by polynucleotides that hybridize under medium-high stringency conditions, high stringency conditions, or very high stringency conditions with (i) the mature polypeptide coding sequence of SEQ ID NO: 1, (ii) the genomic DNA sequence comprising the mature polypeptide coding sequence of SEQ ID NO: 1, or (iii) the full-length complementary strand of (i) or (ii) (J. Sambrook, E. F. Fritsch, and T. Maniatis, 1989, Molecular Cloning, A Laboratory Manual, 2d edition, Cold Spring Harbor, N.Y.).

The polypeptide of the present invention is derived from a strain of *Kinochaeta* sp. The polypeptide has phospholipase C activity, and has activity towards the major phospholipids including phosphatidylcholine, phosphatidylethanolamine, phosphatidic acid and phosphatidyl inositol.

The polynucleotide of SEQ ID NO: 1 or a subsequence thereof, as well as the amino acid sequence of SEQ ID NO: 2 or a fragment thereof, may be used to design nucleic acid probes to identify and clone DNA encoding polypeptides having phospholipase C activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having phospholipase C activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1 or a subsequence thereof, the carrier material is preferably used in a Southern blot.

For purposes of the present invention, hybridization indicates that the polynucleotide hybridizes to a labeled nucleic acid probe corresponding to the mature polypeptide coding sequence of SEQ ID NO: 1; the genomic DNA sequence comprising the mature polypeptide coding sequence of SEQ ID NO: 1; its full-length complementary strand; or a subsequence thereof; under very low to very high stringency conditions. Molecules to which the nucleic acid probe hybridizes under these conditions can be detected using, for example, X-ray film.

In one aspect, the nucleic acid probe is the mature polypeptide coding sequence of SEQ ID NO: 1. In another aspect, the nucleic acid probe is a polynucleotide that encodes the polypeptide of SEQ ID NO: 2 or a fragment thereof. In another preferred aspect, the nucleic acid probe is SEQ ID NO: 1.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), at 50° C. (low stringency), at 55° C. (medium stringency), at 60° C. (medium-high stringency), at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

The present invention also relates to isolated polypeptides having phospholipase C activity encoded by polynucleotides having a sequence identity to the mature polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or even 100%.

The present invention also relates to variants comprising a substitution, deletion, and/or insertion of one or more (or several) amino acids of the mature polypeptide of SEQ ID NO: 2, or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like. Essential amino acids in a parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for phospholipase C activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to the parent polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86:2152-2156; WO 95/17413; or WO 95/22625. Other methods that can be used include error-prone PCR, phage display (e.g., Lowman et al., 1991, *Biochemistry* 30: 10832-10837; U.S. Pat. No.

5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The total number of amino acid substitutions, deletions and/or insertions of the mature polypeptide of SEQ ID NO: 2 is not more than 10, e.g., 1, 2, 3, 4, 5, 6, 7, 8 or 9.

The polypeptide may be hybrid polypeptide in which a portion of one polypeptide is fused at the N-terminus or the C-terminus of a portion of another polypeptide.

The polypeptide may be a fused polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12:2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76:245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6:240-248; and Stevens, 2003, *Drug Discovery World* 4: 35-48.

Sources of Polypeptides Having Phospholipase C Activity

A polypeptide having phospholipase C activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. For example, the polypeptide may be a gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* polypeptide having phospholipase C activity, or a gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasma* polypeptide.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide.

In another aspect, the polypeptide is a *Streptococcus equisimilis, Streptococcus pyogenes, Streptococcus uberis*, or *Streptococcus equi* subsp. *Zooepidemicus* polypeptide.

In another aspect, the polypeptide is a *Streptomyces achromogenes, Streptomyces avermitilis, Streptomyces coelicolor, Streptomyces griseus*, or *Streptomyces lividans* polypeptide.

The polypeptide may also be a fungal polypeptide. For example, the polypeptide may be a yeast polypeptide such as a *Candida, Kluyveromyces, Pichia, Saccharomyces, Schizosaccharomyces*, or *Yarrowia* polypeptide; or a filamentous fungal polypeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Kinochaeta, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide.

In another aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide In another aspect, the polypeptide is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Kinochaeta sp., Kinochaeta pughii, Kinochaeta ramifera, Kinochaeta spissa, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei*, or *Trichoderma viride* polypeptide.

In a preferred embodiment, the polypeptide is derived from a *Kinochaeta* sp.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) using the above-mentioned probes. Techniques for isolating microorganisms from natural habitats are well known in the art. The polynucleotide encoding the polypeptide may then be obtained by similarly screening a genomic or cDNA library of another microorganism or mixed DNA sample. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Polynucleotides

The present invention also relates to isolated polynucleotides encode a polypeptide of the present invention.

The techniques used to isolate or clone a polynucleotide encoding a polypeptide are known in the art and include isolation from genomic DNA, preparation from cDNA, or a combination thereof. The cloning of the polynucleotides from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Kinochaeta* sp, or another or related organism and thus, for example, may be an allelic or species variant of the polypeptide encoding region of the polynucleotide.

The present invention also relates to isolated polynucleotides comprising or consisting of polynucleotides having a degree of sequence identity to the mature polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or even 100%, which encode a polypeptide having phospholipase C activity.

Modification of a polynucleotide encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant may be constructed on the basis of the polynucleotide presented as the mature polypeptide coding sequence of SEQ ID NO: 1, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

The present invention also relates to isolated polynucleotides encoding polypeptides of the present invention, which hybridize under medium-high stringency conditions, high stringency conditions, or very high stringency conditions with (i) the mature polypeptide coding sequence of SEQ ID NO: 1, (ii) the genomic DNA sequence comprising the mature polypeptide coding sequence of SEQ ID NO: 1, or (iii) the full-length complementary strand of (i) or (ii); or allelic variants and subsequences thereof (Sambrook et al., 1989, supra), as defined herein.

In one aspect, the polynucleotide comprises or consists of SEQ ID NO: 1, the mature polypeptide coding sequence of SEQ ID NO: 1, or a subsequence of SEQ ID NO: 1 that encode a fragment of SEQ ID NO: 2 having phospholipase C activity.

Nucleic Acid Constructs

The present invention also relates to nucleic acid constructs comprising a polynucleotide of the present invention operably linked to one or more (several) control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, a polynucleotide that is recognized by a host cell for expression of a polynucleotide encoding a polypeptide of the present invention. The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *Streptomyces coelicolor* agarase gene (dagA), and prokaryotic beta-lactamase gene (VIIIa-Kamaroff et al., 1978, *Proc. Natl. Acad. Sci. USA* 75: 3727-3731), as well as the tac promoter (DeBoer et al., 1983, *Proc. Natl. Acad. Sci. USA* 80:21-25). Further promoters are described in "Useful proteins from recombinant bacteria" in Gilbert et al., 1980, *Scientific American,* 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter including a gene encoding a neutral alpha-amylase in *Aspergilli* in which the untranslated leader has been replaced by an untranslated leader from a gene encoding triose phosphate isomerase in *Aspergilli*; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the host cell of choice may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular. Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (several) convenient restriction sites to allow for insertion or substitution of the polynucleotide encoding the polypeptide at such sites. Alternatively, the polynucleotide may be expressed by inserting the polynucleotide or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more (several) control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any gram-positive or gram-negative bacterium. Gram-positive bacteria include, but not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56:209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (Praha) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-207, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium*

*sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023 and Yelton et al., 1984, *Proc. Natl. Acad. Sci. USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology, Volume* 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Aspergillus*. In a more preferred aspect, the cell is *Aspergillus oryzae*.

The present invention also relates to methods of producing a polypeptide of the present invention, comprising: (a) cultivating a recombinant host cell of the present invention under conditions conducive for production of the polypeptide; and (b) recovering the polypeptide.

The host cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

In an alternative aspect, the polypeptide is not recovered, but rather a host cell of the present invention expressing a polypeptide is used as a source of the polypeptide.

Plants

The present invention also relates to plants, e.g., a transgenic plant, plant part, or plant cell, comprising an isolated polynucleotide of the present invention so as to express and produce the polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide may be constructed in accordance with methods known in the art. In short, the plant or plant cell is constructed by incorporating one or more (several) expression constructs encoding a polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21:285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24:275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338:274).

Presently, *Agrobacterium tumefaciens*-mediated gene transfer is the method of choice for generating transgenic dicots (for a review, see Hooykas and Schilperoort, 1992, *Plant Mol. Biol.* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant J.* 2:275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods for use in accordance with the present disclosure include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct prepared according to the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention, or a portion of a DNA construct prepared in accordance with the present invention. Crossing results in the introduction of a transgene into a plant line by cross pollinating a starting line with a donor plant line. Non-limiting examples of such steps are further articulated in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising: (a) cultivating a transgenic plant or a plant cell comprising a polynucleotide encoding the polypeptide under conditions conducive for production of the polypeptide; and (b) recovering the polypeptide.

Compositions

The present invention also relates to compositions comprising a polypeptide of the present invention. The composition may comprise a polypeptide of the present invention as the major enzymatic component, e.g., a mono-component composition. Alternatively, the composition may comprise additional enzymes, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The further enzyme may also be a polypeptide having phospholipase A1, A2, B and/or D activity. The additional enzyme(s) may be produced, for example, by a microorganism belonging to the genus *Aspergillus*, e.g., *Aspergillus aculeatus*, *Aspergillus awamori*, *Aspergillus foetidus*, *Aspergillus fumigatus*, *Aspergillus japonicus*, *Aspergillus nidulans*, *Aspergillus niger*, or *Aspergillus oryzae*; *Fusarium*, e.g., *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, e.g., *Humicola insolens* or *Humicola lanuginosa*; or *Trichoderma*, e.g., *Trichoderma harzianum*, *Trichoderma koningii*, *Trichoderma longibrachiatum*, *Trichoderma reesei*, or *Trichoderma viride*.

The compositions may be prepared in accordance with methods known in the art and may be in the form of a liquid or a dry composition. For instance, the composition may be in the form of a granulate or a microgranulate. The polypeptide may be stabilized in accordance with methods known in the art.

Uses

The present invention is also directed to methods for using the polypeptides having phospholipase C activity, or compositions thereof.

The phospholipase of the invention may be applied in a process comprising treatment of a phospholipid or lysophospholipid with the phospholipase. Upon contacting with the phospholipase C the phospholipid or lysophospholipid is hydrolysed to yield diglyceride and a phosphate ester, or monoglyceride and a phosphate ester, respectively.

The phospholipase of the invention may be applied in a process comprising degumming of vegetable oil, e.g. an edible vegetable oil, in a process comprising hydrolysis of phospholipids to obtain improved phospholipid emulsifiers, in particular wherein said phospholipid is lecithin, in a process comprising hydrolysis of phospholipids in the gum fraction from water degumming to release entrapped triglyceride oil, in a process for improving the filterability of an aqueous solution or slurry of carbohydrate origin which contains phospholipid, and/or in a process for making a baked product, comprising adding the phospholipase to a dough, and baking the dough to make the baked product.

A polypeptide of the present invention may be used for degumming an aqueous carbohydrate solution or slurry to improve its filterability, particularly, a starch hydrolysate, especially a wheat, starch hydrolysate which is difficult to filter and yields cloudy filtrates. The treatment may be performed using methods well known in the art. See, for example, EP 219,269, EP 808,903.

A polypeptide of the present invention may be used in a process to reduce the phospholipid content in an edible oil. See, for example, WO 2007/103005 and US 2008/0182322. Such a process is applicable to the purification of any edible oil which contains phospholipid, e.g., vegetable oil such as soybean oil, rape seed oil, and sunflower oil.

The phospholipase treatment can be carried out directly in the crude oil or after removal of slime (mucilage) e.g. by wet refining. After wet refining the oil typically will contain 50-250 ppm of phosphorus as phospholipid at the beginning of the treatment with the phospholipase, and the treatment may reduce the phosphorus value, preferably to below 11 ppm, such as to below 5-10 ppm.

The phospholipase treatment is conducted by dispersing an aqueous solution of the phospholipase, preferably as droplets with an average diameter below 10 microM. The amount of water is preferably 0.5-5% by weight in relation to the oil. An emulsifier may optionally be added. Mechanical agitation may be applied to maintain the emulsion. The phospholipase treatment can be conducted at a pH in the range of about 1.5 to about 7.0, preferably 3.5 to about 6. A suitable temperature is generally 30-70° C. (particularly 40-60° C., e.g., 55-55° C.).

The reaction time will typically be 1-12 hours (e.g., 1-6 hours, or 1-3 hours). A suitable enzyme dosage will usually be 0.1-10 mg per liter (e.g., 0.5-5 mg per liter). The phospholipase treatment may be conducted batchwise, e.g., in a tank with stirring, or it may be continuous, e.g., a series of stirred tank reactors. The phospholipase treatment may be followed by separation of an aqueous phase and an oil phase. The separation may be performed by conventional means, e.g., centrifugation. When a liquid lipase is used the aqueous phase will contain phospholipase, and the enzyme may be re-used to improve the process economy.

A polypeptide of the present invention and other such polypeptides having activity towards the four major phospholipids phosphatidylcholine (PC), phosphatidylethanolamine (PE), phosphatidic acid (PA) and phosphatidyl inositol (PI) may be used for degumming an oil composition. Accordingly the invention provides a method for degumming an oil composition, the method comprising (a) providing an oil composition containing a quantity of phospholipids, (b) contacting said oil composition with a phospholipase C enzyme under conditions sufficient for the enzyme to react with the phospholipids to create diacylglycerol and phosphate ester, and, (c) separating the phosphate ester from the oil composition, thereby obtaining a degummed oil composition, wherein the phospholipase C enzyme has activity towards phosphatidylcholine (PC), phosphatidylethanolamine (PE), phosphatidic acid (PA) and phosphatidyl inositol (PI).

In addition to the phospholipase C of the present invention a further enzyme may be applied in the degumming process outlined above. In a preferred embodiment the further enzyme is a polypeptide having phospholipase A1, A2, B and/or D activity. A suitable polypeptide having phospholipase A1 activity may be Lecitase Ultra available from Novozymes A/S. A suitable polypeptide having phospholipase D activity may be e.g., an enzyme derived from *Saccharomyces cerevisiae* and having the sequence UniProt: P36126, or an enzyme derived from *Dictyostelium discoideum* and having the sequence UniProt: Q54Z25.

Furthermore, the invention provides a method of degumming an oil composition, the method comprising (a) providing an oil composition containing a quantity of PC, PE, and/or PI, (b) treating said oil composition with a phospholipase D enzyme to convert PC, PE and/or PI, into PA, (c) treating said oil composition with a phospholipase C enzyme to convert PA in to diglyceride and phosphoric acid. The phospholipase D and phospholipase C may be applied together such that steps (b) and (c) occur substantially simultaneously.

Immobilization of the phospholipase on a suitable carrier may also be applied using any method known in the art incl. by entrapment in natural or synthetic matrices, such as hydrophobic polymers, ion exchanged resins, sol-gels, alginate, and carrageenan; by cross-linking methods such as in cross-linked enzyme crystals (CLEC) and cross-linked enzyme aggregates (CLEA); or by precipitation on salt crystals such as protein-coated micro-crystals (PCMC).

In certain embodiments the present invention relates to a method of producing a fatty acid ester product, wherein the carrier is a hydrophilic carrier selected from the group containing: porous in-organic particles composed of alumina, silica and silicates such as porous glass, zeolites, diatomaceous earth, bentonite, vermiculite, hydrotalcite; and porous organic particles composed of carbohydrate polymers such as agarose or cellulose. In other embodiments the present invention relates to a method of producing a fatty acid ester product, wherein the carrier is a hydrophobic polymeric carrier, e.g. polypropylen, polyethylene, acrylate. Suitable commercial carriers are e.g. LEWATIT™, ACCUREL™, PUROLITE™ and AMBERLITE™.

The present invention is further described by the following examples that should not be construed as limiting the scope of the invention.

Materials and Methods
Phospholipase C Assay:

Reaction mixtures comprising 10 microL of a 100 mM p-nitrophenyl phosphoryl choline (p-NPPC) solution in 100 mM Borax-HCl buffer, pH 7.5 and 90 microL of the enzyme solution are mixed in a microtiter plate well at ambient temperature. The microtiter plate is then placed in a microtiter plate reader and the released p-nitrophenol is quantified by measurement of absorbance at 410 nm. Measurements are recorded during 30 min at 1 minute intervals. Calibration curves in the range 0.01-1 microL/ml p-nitrophenol are prepared by diluting a 10 micromol/ml p-nitrophenol stock solution from Sigma in Borax-HCl buffer. One unit will liberate 1.0 micromol/minute of p-NPPC at ambient temperature.

EXAMPLES

Example 1

Molecular Weight

For determining the molecular weight of the phospholipase C shown in SEQ ID NO: 2, 30 microL of purified enzyme samples were applied to 12% SDS-polyacrylamide gel electrophoresis. The gel was run at 100 V for 1.5 hrs and stained with Coomassie blue. The molecular weight of the enzyme was determined to approximately 65 KDa.

Example 2

Phospholipase C Activity

Concentrated cell-free fermentation broth comprising the phospholipase C shown in SEQ ID NO:2 was diluted in Borax-HCl buffer and the phospholipase C activity was measured using p-NPPC assay. The activity of the enzyme concentrate towards p-NPPC was determined to 0.316 units/ml undiluted sample.

Example 3

Determination of pH-Profile

Phospholipase C (PLC) activity was measured using the assay described in WO2005040410 with the modification that linoleic acid hydroperoxide when formed is detected directly by kinetic measurements at 234 nm. DLPC (1,2-dilinoleoyl-sn-glycero-3-phosphocholine) as substrate is homogenized at 1 mM with 0.25 mM triolein at 60° C. for 1 minute in 40 mM buffer with 2 mM beta-cyclodextrin and 0.8 mM $CaC_2$ prior to cooling to 25° C. and mixing with purified lipoxygenase (from *Magnaporthe salvinii* (WO2002086114)) as well as purified acylglycerol lipase (*Thermomyces lanuginosus*, Lipolase™ from Novozymes A/S) both added in excess (A280=0.04). The final concentration of DLPC is 0.6 mM. Neither *Magnaporthe* lipoxygenase nor *Thermomyces* acylglycerol lipase has notable activity towards DLPC, however upon addition of an enzyme with PLC-activity DLPC is hydrolysed into phosphocholine and 1,2-dilinoylglycerol, the latter is in presence of excess acylglycerol lipase rapidly hydrolyzed into linoleic acid which is a substrate for the lipoxygenase. In short, the presence of PLC-activity results in production of hydroperoxides which is detected at 234 nm. The PLC activity is determined from the maximal average slope (dA234/dt) over 4 minutes during the first 10 minutes of reaction.

The results are shown in table 1.

TABLE 1

| pH-profile; pH-optimum is 100%. | | |
|---|---|---|
| pH | PLC of SEQ ID NO: 2 | Purifine |
| 4.1* | 18% | 11% |
| 5.1* | 46% | 26% |
| 6.1* | 100% | 59% |
| 7.0** | 20% | 100% |
| 8.0** | 4% | 40% |

*Buffer Citrate,
**Buffer Hepes

The phospholipase C shown in SEQ ID NO: 2 had a lower pH-optimum and higher relative activity towards DLPC than Purifine at pH 4-6.

Example 4

Determination of Substrate Specificity

Substrate specificity for phosphatidylcholine (PC), phosphatidylethanolamine (PE), phosphatidic acid (PA) and phosphatidyl inositol (PI) of enzymes with PLC-activity was evaluated using the assay described in Example 3 with the following changes:
Buffer: MES, pH 5.5.
Dose of PLC-enzyme: A280=0.0004
Substrate: 0.6 mM DLPX (DLPC, DLPA, DLPE and DLPI) mixed with 0.15 mM Trilinolein.

The results are shown in table 2.

TABLE 2

| Substrat specificity of PLC of SEQ ID NO: 2 and of Purifine | | | | |
|---|---|---|---|---|
| | DLPI | DLPA | DLPC | DLPE |
| PLC of SEQ ID NO: 2 | 16% | 14% | 100% | 28% |
| Purifine | −1% | 1% | 100% | 2% |

Both enzymes had DLPC as their preferred substrate, however the PLC of SEQ ID NO:2 had a broader specificity and significant activity towards all classes of phospholipids tested. The broad specificity is an advantage in degumming as the enzyme has activity towards all the major phosphatides in vegetable oil.

Example 5

Determination of Thermostability by Differential Scanning Calorimetry

The thermostability of the PLC of SEQ ID NO:2 was determined by Differential Scanning Calorimetry (DSC)

using a VP-Capillary Differential Scanning Calorimeter (MicroCal Inc., Piscataway, N.J., USA). The thermal denaturation temperature, Td (° C.), was taken as the top of denaturation peak (major endothermic peak) in thermograms (Cp vs. T) obtained after heating enzyme solutions in buffer (50 mM Na-acetate pH 5.0 with- or without 5 mM EDTA added) at a constant programmed heating rate of 200 K/hr.

Sample- and reference-solutions (approx. 0.2 ml) were loaded into the calorimeter (reference: buffer without enzyme) from storage conditions at 10° C. and thermally pre-equilibrated for 20 minutes at 20° C. prior to DSC scan from 20° C. to 110° C. Denaturation temperatures were determined with an accuracy of approximately +/−1° C. The results are shown in Table 3 below.

TABLE 3

| Thermostability determined by Differential Scanning Calorimetry | | |
|---|---|---|
| | pH 5 | pH 5 + EDTA |
| PLC of SEQ ID NO: 2 | 78 C. | 78° C. |
| Purifine | 85 C. | 42° C. |

Thermostability was assessed by DSC at pH 5 for Purifine and the PLC of SEQ ID NO:2 with and without 5 mM EDTA. Without EDTA Purifine was slightly more thermostable than the PLC of SEQ ID NO:2. However, whereas the presence of 5 mM EDTA did not affect thermostability of the PLC of SEQ ID NO:2 negatively, Purifine was destabilized by more than 40° C. in the presence of EDTA, indicating a relatively loose binding of catalytically/structurally important divalent metaion(s) in Purifine. The high stability of the PLC of SEQ ID NO:2 in the presence of EDTA indicates high stability under industrial conditions.

Example 6

Degumming of Soy Bean Oil

A test substrate was produced from soy bean oil spiked with the phospholipids PC, PI, PE and PA. The substrate comprised 50 mg phospholipids per 1 mL oil. Samples of 1 mL oil were incubated with 1 mg purified enzyme protein in a thermoshaker at 45° C. Besides the enzymatic reactions, a blank reaction was incubated, in which the enzyme solution was replaced with addition of water.

The samples were analyzed by $^{31}$P NMR. The principle of the NMR-based assay is that the phosphate will leave the oil phase after PLC action on the phospholipids. Hence, the NMR integrals of the oil phase will become smaller upon enzymatic action. A blank was included to compensate for non-enzymatic water degumming.

Results:
45° C., pH 6.0
Sample: Control
Integral size

| | min | | | |
|---|---|---|---|---|
| | 10 | 30 | 60 | 120 |
| PA | 16.36 | 16.36 | 13.34 | 14.43 |
| PE | 32.07 | 32.07 | 24.89 | 26.74 |
| PI | 46.73 | 46.73 | 34.12 | 40.83 |
| PC | 36.53 | 36.53 | 24.39 | 29.21 |
| IS (TPP) | 100 | 100 | 100 | 100 |

Sample: PLC of SEQ ID NO:2
Integral size

| | min | | | |
|---|---|---|---|---|
| | 10 | 30 | 60 | 120 |
| PA | 10.75 | 12.19 | 2.12 | 5.19 |
| PE | 24.7 | 24.65 | 10.24 | 9.5 |
| PI | 30.08 | 21.63 | 6.11 | 8.2 |
| PC | 29.58 | 24.22 | 14.21 | 8.21 |
| IS (TPP) | 100 | 100 | 100 | 100 |

% residual phospholipids
Integral ratios

| | min | | | |
|---|---|---|---|---|
| | 10 | 30 | 60 | 120 |
| PA | 66 | 75 | 16 | 36 |
| PE | 77 | 77 | 41 | 36 |
| PI | 64 | 46 | 18 | 20 |
| PC | 81 | 66 | 58 | 28 |
| IS (TPP) | 100 | 100 | 100 | 100 |

45° C., pH 4.0
Sample: Control
Integral size

| | min | | | |
|---|---|---|---|---|
| | 10 | 30 | 60 | 120 |
| PA | 18.59 | 14.18 | 14.51 | 10.99 |
| PE | 36.91 | 28.5 | 30.06 | 24.77 |
| PI | 50.77 | 37.73 | 40.94 | 30.25 |
| PC | 35.82 | 28.43 | 30.49 | 21.67 |
| IS (TPP) | 100 | 100 | 100 | 100 |

Sample: PLC of SEQ ID NO:2
Integral size

| | min | | | |
|---|---|---|---|---|
| | 10 | 30 | 60 | 120 |
| PA | 14.4 | 10.1 | 5.64 | 2.83 |
| PE | 31.12 | 23.65 | 18.07 | 8.88 |
| PI | 33.81 | 18.13 | 8.57 | 4.31 |
| PC | 31.74 | 24.19 | 16.84 | 7.33 |
| IS (TPP) | 100 | 100 | 100 | 100 |

% residual phospholipids
Integral ratio

| | min | | | |
|---|---|---|---|---|
| | 10 | 30 | 60 | 120 |
| PA | 77 | 71 | 39 | 26 |
| PE | 84 | 83 | 60 | 36 |
| PI | 67 | 48 | 21 | 14 |
| PC | 89 | 85 | 55 | 34 |
| IS (TPP) | 100 | 100 | 100 | 100 |

The PLC shown in SEQ ID NO:2 had activity on all four phospholipids at pH 6.0 as well as at pH 4.0.

The invention claimed is:

1. A nucleic acid construct comprising a polynucleotide encoding a polypeptide having phospholipase C activity, wherein the polynucleotide is operably linked to one or more heterologous control sequences that direct expression of the polypeptide in an expression host cell, and wherein the amino acid sequence of the polypeptide having phospholipase C activity is selected from the group consisting of:
   (a) an amino acid sequence with at least 90% sequence identity to the sequence of amino acids 1 to 625 of SEQ ID NO: 2 and
   (b) a fragment of the sequence of amino acids 1 to 625 of SEQ ID NO: 2 that has phospholipase C activity.

2. A microbial recombinant host cell comprising the nucleic acid construct of claim 1.

3. A method of producing a polypeptide having phospholipase C activity, comprising:
   (a) cultivating the microbial recombinant host cell of claim 2 under conditions conducive for production of the polypeptide having phospholipase C activity; and
   (b) recovering the polypeptide.

4. The nucleic acid construct of claim 1, wherein the polypeptide having phospholipase C activity has an amino acid sequence with at least 95% sequence identity to the sequence of amino acids 1 to 625 of SEQ ID NO: 2.

5. The nucleic acid construct of claim 1, wherein the polypeptide having phospholipase C activity has an amino acid sequence with at least 97% sequence identity to the sequence of amino acids 1 to 625 of SEQ ID NO: 2.

6. The nucleic acid construct of claim 1, wherein the polypeptide having phospholipase C activity comprises the sequence of amino acids 1 to 625 of SEQ ID NO: 2.

7. The nucleic acid construct of claim 1, wherein the polypeptide having phospholipase C activity is encoded by a polynucleotide that hybridizes with the full complementary sequence of nucleotides 55 to 1929 of SEQ ID NO: 1 under very high stringency conditions, wherein the very high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 70° C.

* * * * *